(12) United States Patent
Seshadri et al.

(10) Patent No.: US 10,793,513 B2
(45) Date of Patent: Oct. 6, 2020

(54) PROCESS FOR ELECTROCHEMICAL SEPARATION OF ENANTIOMERS OF AN AMINO ACID FROM A RACEMIC MIXTURE

(71) Applicant: SRM UNIVERSITY, Kancheepuram (IN)

(72) Inventors: Harinipriya Seshadri, Chennai (IN); Samanwita Pal, Chennai (IN); Deepak Kumar, Chennai (IN)

(73) Assignee: SRM UNIVERSITY, Kancheepuram (IN)

( * ) Notice: Subject to any disclaimer, the term of this patent is extended or adjusted under 35 U.S.C. 154(b) by 0 days.

(21) Appl. No.: 16/078,522

(22) PCT Filed: Feb. 25, 2017

(86) PCT No.: PCT/IB2017/051107
§ 371 (c)(1),
(2) Date: Aug. 21, 2018

(87) PCT Pub. No.: WO2017/145124
PCT Pub. Date: Aug. 31, 2017

(65) Prior Publication Data
US 2019/0047941 A1 Feb. 14, 2019

(30) Foreign Application Priority Data
Feb. 26, 2016 (IN) .............................. 201641006824

(51) Int. Cl.
*C07C 227/34* (2006.01)
*C07B 57/00* (2006.01)
(Continued)

(52) U.S. Cl.
CPC ............ *C07C 227/34* (2013.01); *C07B 57/00* (2013.01); *C07C 229/08* (2013.01); *C25B 3/00* (2013.01);
(Continued)

(58) Field of Classification Search
None
See application file for complete search history.

(56) References Cited

U.S. PATENT DOCUMENTS

2010/0266896 A1* 10/2010 Stromme .............. H01M 4/137
429/209

FOREIGN PATENT DOCUMENTS

WO 2005088292 * 9/2005

OTHER PUBLICATIONS

Deepal Kumar et al "Separation of Enantiomers of Alanine from Racemic Mixture by Polycrystalline Metal Surfaces—A Spectroelectrochemical Approach" ECS Transactions, vol. 66 No. 32, 33-43, May 13, 2015.

(Continued)

*Primary Examiner* — Clinton A Brooks
*Assistant Examiner* — Jennifer C Sawyer
(74) *Attorney, Agent, or Firm* — The Roy Gross Law Firm, LLC; Roy Gross

(57) ABSTRACT

The present disclosure relates to a process for separation of enantiomers of the amino acid from a racemic mixture. The process comprises electrolyzing the first electrolyte having 1 molar solution of lithium perchlorate and 0.01 molar solution of racemic mixture of amino acid in an electrochemical cell containing a working electrode having polycrystalline metal surface configured to adsorb L-enantiomer of amino acid using a saw-tooth current. Further, the polarity of the saw-tooth current is reversed to de-adsorb the L-enantiomer of amino acid from the working electrode into the second electrolyte re-filled in the cell. The process of the present disclosure to separate enantiomer of amino acid from a racemic mixture is simple and economical.

5 Claims, 5 Drawing Sheets

Potential (V)

(51) Int. Cl.
*C07C 229/08* (2006.01)
*C25B 3/00* (2006.01)
*C25B 11/04* (2006.01)
*C25B 15/08* (2006.01)

(52) U.S. Cl.
CPC ............ *C25B 11/041* (2013.01); *C25B 15/08* (2013.01); *C07B 2200/07* (2013.01)

(56) References Cited

OTHER PUBLICATIONS

International Search Report PCT/IB2017/051107 Completed Apr. 26, 2017; dated Apr. 26, 2017 2 pages.
Written Opinion of the International Searching Authority PCT/IB2017/051107 dated Apr. 26, 2017 5 pages.

* cited by examiner

PROCESS FOR ELECTROCHEMICAL SEPARATION OF ENANTIOMERS OF AN AMINO ACID FROM A RACEMIC MIXTURE

RELATED APPLICATIONS

This application is a National Phase of PCT Patent Application No. PCT/IB2017/051107 having International filing date of Feb. 25, 2017, which claims the benefit of priority of Indian Patent Application No. 201641006824 filed on Feb. 26, 2016. The contents of the above applications are all incorporated by reference as if fully set forth herein in their entirety.

FIELD

The present disclosure relates to a process for separation of enantiomers of an amino acid from a racemic mixture.

Definitions

As used in the present disclosure, the following terms are generally intended to have the meaning as set forth below, except to the extent that the context in which they are used indicate otherwise.

The term 'IVIUMSTAT' refers to the Potentiostat manufactured by Ivium technologies.

The term 'Electrochemical cell' refers to a cell which comprises a vessel for holding an electrolyte, a working electrode, a reference electrode, and an auxiliary electrode that are dipped in an electrolyte, and the working, the reference, and the auxiliary electrodes are connected to a saw-tooth generator capable of generating a saw-tooth current to the electrodes.

The term 'Polycrystalline' refers to an aggregate of very small crystals in random orientations.

The term 'Salting out' refers to an effect based on the electrolyte-nonelectrolyte interaction, in which the non-electrolyte could be less soluble at high salt concentrations.

BACKGROUND

Stereoisomers are molecules that differ from each other only in the arrangement of their atoms in space. Stereoisomers are generally classified as diastereomers and enantiomers. Enantiomers are mirror images of each other and particularly one enantiomer of a molecule is often physiologically active, while the other enantiomer may be either inactive or toxic. Distinguishing enantiomers, such as amino acids, have important applications in analytical chemistry, biotechnology, and medical sciences; this is because, different enantiomers exhibit different biological activities and different therapeutic properties. Sometimes one enantiomer shows bio-activity, while the other is inert or even harmful.

The synthetic techniques usually used to produce enantiomers, generate a mixture and not pure enantiomers. Hence, before further use, there is a need to separate the enantiomer of interest.

Conventional methods for separating enantiomers include capillary zone electrophoresis, diastereomeric resolutions, enzyme catalysed reactions, chromatographic methods, methods using liquid membranes, molecular recognition techniques, and inclusion complexation methods. However, the major drawback of the conventional methods is that large quantities of optically pure chiral reagents or solvents are required, which are expensive and are not recoverable. Enantioselective chiral columns, having chiral stationary phases, are costly and have a limited working life, which in turn increases the cost of separation.

There is, therefore, felt a need of a simple and economic process for separating enantiomers of amino acid from racemic mixture.

OBJECTS

Some of the objects of the present disclosure, which at least one embodiment herein satisfies, are as follows:

It is an object of the present disclosure to ameliorate one or more problems of the prior art or to at least provide a useful alternative.

It is an object of the present disclosure to provide a process for electrochemical separation of enantiomers of amino acid from racemic mixture.

It is another object of the present disclosure to provide a simple and economical process for electrochemical separation of enantiomers of amino acid from racemic mixture.

Other objects and advantages of the present disclosure will be more apparent from the following description, which is not intended to limit the scope of the present disclosure.

SUMMARY

The present disclosure provides a process for separating the enantiomers of an amino acid, selected from alanine and methionine, from a racemic mixture of the amino acid. The process comprises mixing of 0.01 molar solution of the racemic amino acid with 1 molar solution of lithium perchlorate to form a first electrolyte. The first electrolyte is electrolyzed, using a saw-tooth current, in an electrochemical cell in which the working electrode has a polycrystalline metal surface configured to adsorb the L-enantiomer of said amino acid and retaining the D-enantiomer of said amino acid in the first electrolyte. The first electrolyte containing D-enantiomer is drained from the cell. The D-enantiomer is separated from the first electrolyte. The drained cell having the working electrode with the adsorbed L-enantiomer is re-filled with a second electrolyte containing sodium chloride. The polarity of the saw-tooth current fed to the cell is reversed to de-adsorb the L-enantiomer from the working electrode into the second electrolyte. The second electrolyte having the L-enantiomer is drained. The L-enantiomer is separated from the second electrolyte.

BRIEF DESCRIPTION OF ACCOMPANYING DRAWINGS

DETAILED DESCRIPTION

Figure 1:
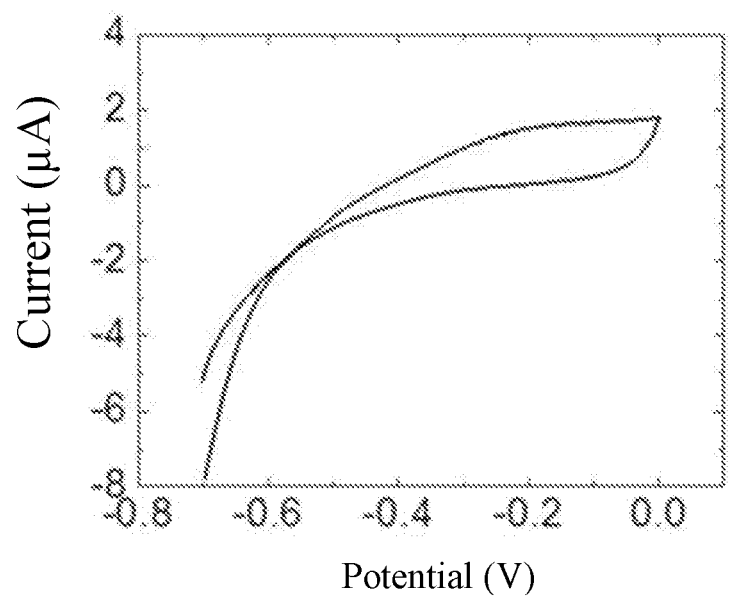
FIG. 1 illustrates the cyclic voltammogram of 0.01M racemic alanine in 1M lithium perchlorate solution on Nickel electrode surface.

Separation of enantiomers is a critical problem for chemists/or in a particular industry. Enantiomers have same properties such as boiling points, melting points, solubilities, and the like, hence the separation of enantiomers is a difficult task, and moreover it is expensive. Separation of enantiomers is important, especially when it comes to biological systems, because they may exhibit different biological activity. Therefore, it is important to develop a system and a method for chiral separation of enantiomers, in order to eliminate the unwanted enantiomer and recover the wanted one. The present disclosure, therefore, envisages a system and a method for electrochemical separation of the enantiomers, typically of alanine and methionine, economically and effectively.

In an embodiment of the present disclosure, there is provided a process for separating the enantiomers of an amino acid, selected from alanine and methionine, from a racemic mixture of the amino acid. The process comprising the following step:

In the first step, 0.01 molar solution of the racemic amino acid is mixed with 1 molar solution of lithium perchlorate to form a first electrolyte.

In an embodiment of the present disclosure, the racemic mixture of the amino acid comprises 0.005 molar solution of L-enantiomer of the amino acid and 0.005 molar solution of D-enantiomer of the amino acid.

In the second step, the first electrolyte is electrolyzed, using a saw-tooth current, in an electrochemical cell in which the working electrode has a polycrystalline metal surface configured to adsorb the L-enantiomer of the amino acid and retaining the D-enantiomer of the amino acid in the first electrolyte.

In an embodiment of the present disclosure, the working electrode having polycrystalline metal surface can be at least one selected from the group consisting of silver (Ag), gold (Au), cadmium (Cd), and nickel (Ni). The polycrystalline metal surface provides a chiral center for adsorption of enantiomers of the amino acid from the racemic mixture of the amino acid.

Particularly, the saw-tooth current or wave is transmitted to the electrochemical cell as pulse such as 50 mV/s and falls to zero and again starts as pulse in the forward scan. This results in electrolysis in the electrochemical cell and deposition of one of the amino acid enantiomers on the surface of the working electrode having polycrystalline metal surface. In accordance with one embodiment of the present disclosure, in the forward scan the pulse ranges from −1 V/s to 1 V/s and in the reverse scan the pulse ranges from 1 V/s to −1 V/s.

In the third step, the first electrolyte containing D-enantiomer is drained from the cell.

In the fourth step, the D-enantiomer is separated from the first electrolyte.

In an embodiment of the present disclosure, the D-enantiomer of the amino acid is separated by any one of the techniques selected from the group consisting of evaporation, solvent separation, and salting out.

In the fifth step, the drained cell having the working electrode with the adsorbed L-enantiomer is re-filled with a second electrolyte containing sodium chloride.

In an embodiment of the present disclosure, the solution of sodium chloride is used as a second electrolyte.

Typically, the electrolyte is capable of conducting cationic and anionic charge carriers.

In the sixth step, the polarity of the saw-tooth current fed to the cell is reversed to de-adsorb the L-enantiomer from the working electrode into the second electrolyte.

In the seventh step, the second electrolyte having the L-enantiomer is drained.

In the eighth step, the L-enantiomer is separated from the second electrolyte. In an embodiment of the present disclosure, the L-enantiomer is separated by any one of the techniques selected from the group consisting of evaporation, solvent separation, and salting out.

In accordance with an embodiment of the present disclosure, the system for electrochemical separation of enantiomers comprises an electrochemical cell. The electrochemical cell comprises a working electrode, a reference electrode, and an auxiliary electrode, wherein the electrodes are dipped in an electrolyte and the electrodes are connected to a saw-tooth generator capable of generating a saw-tooth current to the electrodes.

In accordance with an embodiment of the present disclosure, the reference electrode can be at least one selected from the group consisting of a saturated calomel electrode (SCE), mercury/mercurous sulphate, alkaline/mercurous oxide, and silver (Ag)/silver chloride (AgCl).

In accordance with an embodiment of the present disclosure, the auxiliary electrode can be at least one of graphite, and platinum. Particularly, no current flows through the auxiliary electrode and it is generally used as ohmic resistance.

In accordance with the present disclosure, the working electrode having polycrystalline metal surface, the reference electrode, and the auxiliary electrode can be polished with alumina solution.

The system of the present disclosure further comprises a potentiostat, wherein the potentiostat is configured to apply potential to the working electrode having polycrystalline metal surface. Typically, the potential control range can be ±1V and the scan rate can be 50 mV/s. The program used in the processing unit allows a rapid data acquisition and an easy data analysis. The program typically contains a fast digital function generator and a high speed data acquisition circuitry.

The system of the present disclosure further comprises a memory, for example—an intransient memory, wherein the memory is connected to the processing unit. Particularly, the polarity reversal occurs as a result of predefined rules stored in the intransient memory that is linked to the processing unit so as to increase the separation and deposition (yield) of a desired enantiomer of the amino acid.

In accordance with the present disclosure, the processing unit monitors the threshold/excessive level of anodic oxidation occurring at the working electrode and switches the polarity of the saw-tooth current accordingly.

In accordance with the present disclosure, the method comprises a process cycle and a reverse cycle.

In the process cycle, the saw-tooth current is transmitted to the electrochemical cell under forward scan, i.e., a potential across the electrochemical cell is applied to cause the working electrode having polycrystalline metal surface to act as an anode and the second electrode (reference electrode) to act as a cathode, which in turn electrolyzes the enantiomeric solution.

In the reverse cycle, the polarity of the current is reversed. The reverse cycle is performed once a desired threshold level or excessive level of anodic oxidation is reached. The reverse cycle is carried out by supplying the saw-tooth current to the electrodes under reverse polarity, thereby causing the working electrode to act as a cathode and reducing the anodic oxidation. This results in reactivation of the working electrode.

The product yield obtained using the process of the present disclosure is of at least 64%.

The process of the present disclosure reactivates the polycrystalline metal surfaces of the working electrode so that these electrodes can be reused. Further, the amount of chiral reagents or solvents required in the system of the present disclosure is less. The product yield recovered from the process of the present disclosure is high. Hence, the process of the present disclosure is simple, economical, and productive.

In accordance with the present disclosure, an IVIUM-STAT spectroelectrochemical workstation known as cyclic voltammetry can be used to deposit L-enantiomer of the amino acid with lithium perchlorate ($LiClO_4$), as an electrolyte, onto the working electrode.

The present disclosure is further described in light of the following experiments which are set forth for illustration purpose only and not to be construed for limiting the scope of the disclosure. The following laboratory scale experiments can be scaled up to industrial/commercial scale.

EXPERIMENTAL DETAILS

Experiment 1: Process for Electrochemical Separation of Enantiomers of Alanine Using Nickel Electrode Surface 1M lithium perchlorate ($LiClO_4$) solution was mixed with the solution of 0.01M racemic alanine to form a first electrolyte. 0.01M racemic alanine consists of 0.005M D-alanine (50%) and 0.005M L-alanine (50%). The so formed first electrolyte was taken in an electrochemical cell which was further connected to the potentiostat. The electrochemical cell consists of working electrode i.e., Nickel electrode while silver (Ag)/silver chloride (AgCl) was used as reference electrode. The platinum coil worked as the auxiliary electrode. The working, reference, and auxiliary electrodes were polished with alumina solution before starting the measurements. The diameter of the electrode was 1 mm. The pH of the 1M lithium perchlorate ($LiClO_4$) solution containing 0.01M racemic alanine was maintained at 6.5. An IVIUMSTAT spectroelectrochemical workstation (Cyclic voltammetry) was employed for recording cyclic voltammogram (CV) of 0.01M racemic alanine in 1M lithium perchlorate ($LiClO_4$) solution. The enantiomeric separation process was carried out at room temperature. The so formed first electrolyte was electrolyzed in the electrochemical cell using saw-tooth current which leads to the adsorption of L-alanine on Nickel electrode surface (working electrode) and obtains first electrolyte with D-alanine in the cell. Further, the so obtained first electrolyte containing D-alanine was drained from the cell, followed by evaporation to separate D-alanine from the first electrolyte. Further, the drained electrochemical cell was re-filled with the solution of sodium chloride as second electrolyte. The polarity of the saw-tooth current was reversed to de-adsorb the L-alanine from said Nickel electrode surface into the second electrolyte. The second electrolyte having L-alanine was drained, followed by evaporation to separate L-alanine from the second electrolyte.

The voltammogram was recorded at −0.6 V at the scan rate of 50 mV/s. In this arrangement the Nickel electrode acts as anode and reference electrode acts as cathode which in turn electrolyzes the racemic alanine present in 1M lithium perchlorate in the electrochemical cell. This results in the deposition of L-alanine on the surface of the Nickel electrode.

The CV as represented in FIG. 1 illustrate no significant peak currents both on anodic and cathodic scan indicating only ion and mass transfer and hence a gap between cathodic and anodic scan was noticed. This could be attributed to the fact that the Nickel surface was initially covered by L-alanine and gets de-adsorbed in the cathodic scan without significant adsorption/oxidation of the surface or reduction.

Experiment 2: Process for Electrochemical Separation of Enantiomers of Alanine Using Silver Electrode Surface The process for electrochemical separation of enantiomers of alanine is similar to the process of the experiment 1 of the present disclosure except Silver electrode surface was used instead of Nickel electrode surface.

Figure 2:
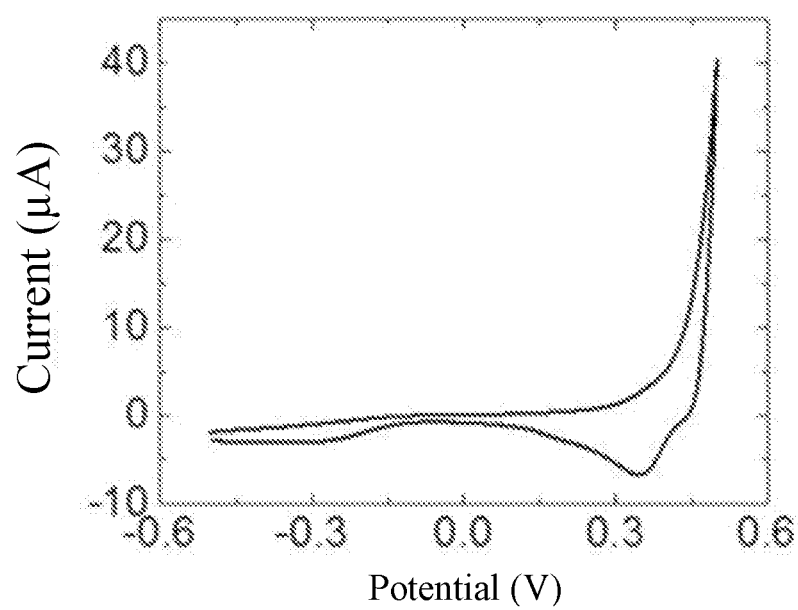
FIG. 2 illustrates the cyclic voltammogram of 0.01M racemic alanine in 1M lithium perchlorate solution on Silver electrode surface.

The CV as represented in FIG. 2 illustrate no significant current throughout the applied potential range, indicating the absence of oxidation of the species or surface inhibition by adsorbed L-alanine molecules. In the reverse potential sweep, first cathodic peak current was observed at 0.35V and this could be attributed to the reduction of adsorbed L-alanine molecules on the silver surface. In the subsequent potential sweep, a small peak current was noticed at −0.3 V which is approximately 600 mV more negative than that for the first reduction peak. This clearly indicated that the oxidized species ($CH_3$—$CH(NH_3+)COOH$) was getting reduced on the reverse potential sweep resulting in several by products.

Experiment 3: Process for Electrochemical Separation of Enantiomers of Alanine Using Gold Electrode Surface The process for electrochemical separation of enantiomers of alanine is similar to the process of the experiment 1 of the present disclosure except Gold electrode surface was used instead of Nickel electrode surface.

Figure 3:
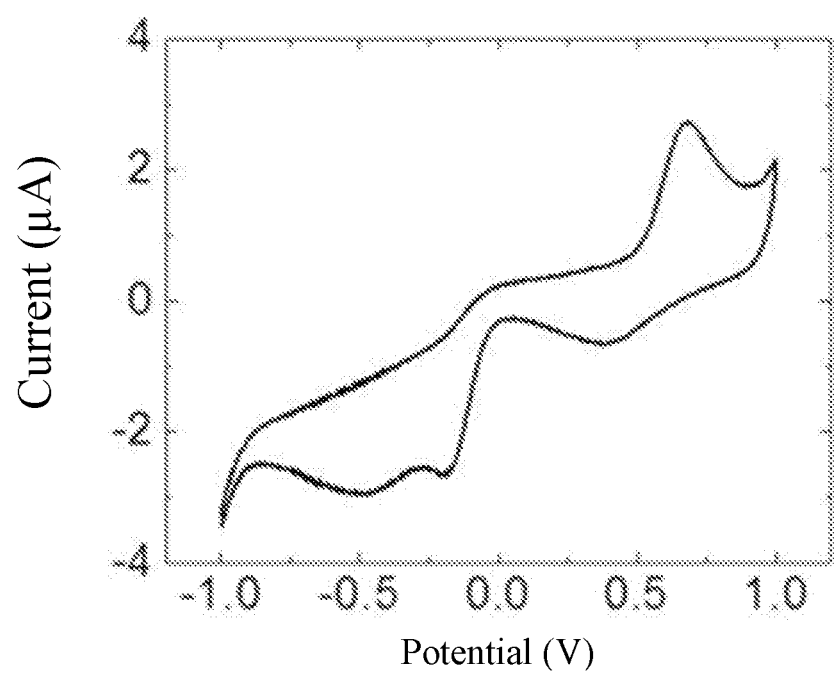
FIG. 3 illustrates the cyclic voltammogram of 0.01M racemic alanine in 1M lithium perchlorate solution on Gold electrode surface.

The CV as represented in FIG. 3 illustrates two consecutive current peaks in the anodic scan, the first one at 0V and the second one at 0.72V respectively. These two peaks can be ascribed to the oxidation of adsorbed L-alanine and oxidation of the Gold surface respectively. The peak current of the first peak is very low in comparison with that of the second peak. This trend in peak currents indicated that oxidation of Gold surface was much more predominant than the oxidation of adsorbed L-alanine species. In the reverse potential sweep, four peak currents were observed, first at 0.9V, second at 0.4V, third at −0.15V and the fourth at −0.5V. The second peak was 500 mV negative to the first peak indicating reduction of adsorbed alanine leading to several byproducts. This clearly indicated that the oxidized species ($CH_3$—$CH(NH_3+)COOH$) were getting reduced on the reverse potential sweep resulting in several by products. The fourth peak was 350 mV negative to the third peak. These two peaks correspond to the further reduction of the byproducts.

Experiment 4: Process for Electrochemical Separation of Enantiomers of Alanine Using Cadmium Electrode Surface The process for electrochemical separation of enantiomers of alanine is similar to the process of the experiment 1 of the present disclosure except Cadmium electrode surface was used instead of Nickel electrode surface.

Figure 4:
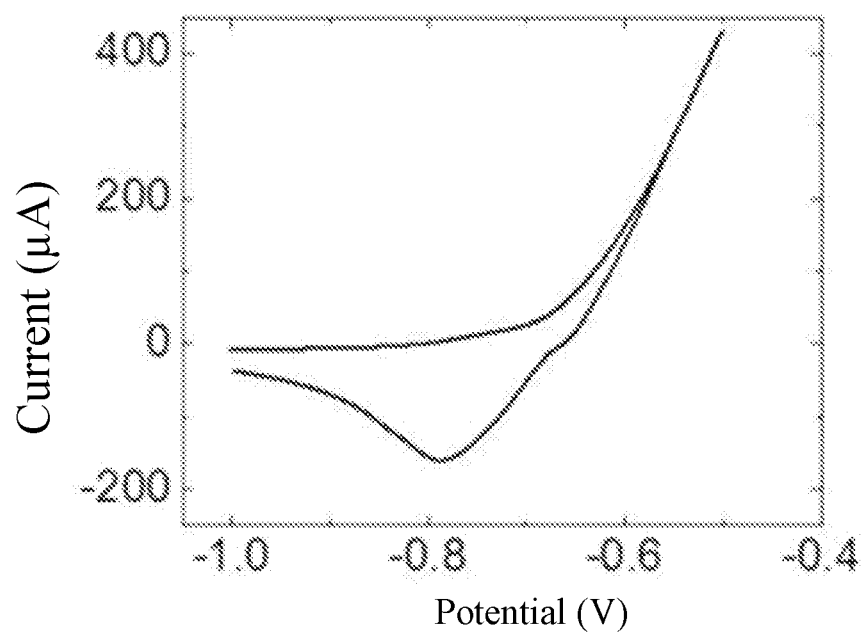
FIG. 4 illustrates the cyclic voltammogram of 0.01M racemic alanine in 1M lithium perchlorate solution on Cadmium electrode surface.

The CV as represented in FIG. 4 showed no significant anodic peak current depicting the absence of oxidation of adsorbed L-alanine and oxidation of Cadmium surface. This behavior was analogous to L-alanine behavior on silver surface (FIG. 1). In the reverse potential sweep two current peaks first at −0.75V and second at −0.79V were observed. The second peak was 50 mV negative to the first, depicting the reduction of adsorbed alanine molecules on Cadmium surface resulting in byproducts. This trend in reduction peaks was identical to the reduction peak trend on silver surface. The main difference between the behavior of L-alanine on Silver and Cadmium was the shift in peaks from more positive potential to negative potential. This anomalous behavior of L-alanine on Silver and Cadmium could be attributed to different end products and byproducts.

It is evident from the experiment 1 to 4 that an order of degradation or formation of more byproducts from comparative CV analysis is as follows: Gold electrode surface>Silver electrode surface, Cadmium electrode surface>Nickel electrode surface.

Experiment 5: Characterization Study of 0.01 M Racemic Alanine in Lithium Perchlorate Before and After CV Analysis with Different Metal Electrodes The Circular Dichroism (CD) spectra of the freshly prepared 0.01 M racemic alanine in 1M lithium perchlorate and solutions after Cyclic voltammetric studies were recorded in nitrogen atmosphere in the wavelength range of 200 to 300 nm. The nitrogen purging rate of 5 liter/minute was maintained throughout the experiments. A scan rate of 20 nm/minute was used.

Figure 5:
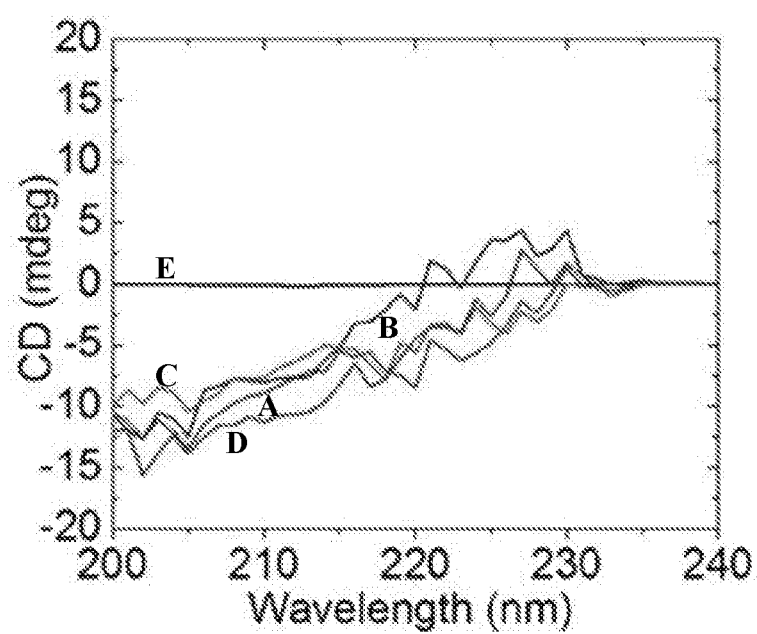
FIG. 5 illustrates the circular dichroism spectra of 0.01 M racemic alanine in 1M lithium perchlorate before and after cyclic voltammetry analysis with different metal electrodes.

Graph (E) of the FIG. 5 depicts that there was no rotation for freshly prepared 0.01 M racemic alanine in 1M lithium perchlorate.

The Circular Dichroism (CD) spectra recorded for after the CV studies of alanine on different metal surfaces revealed more negative rotation, thereby indicating the dextrorotation of the alanine containing 1M lithium perchlorate solution (First electrolyte) after electrochemical studies. Thus CV perturbation on racemic alanine induced preferential adsorption of L-alanine on the metal surfaces and hence the concentration of D-alanine was higher in the 1M lithium perchlorate solution. In the present disclosure, the peak appeared at 205 nm was considered as the alanine peak which exhibited low intensity i.e., −13.46 mdeg on Silver metal surface [graph (A) of FIG. 5], −12.42 mdeg on Gold metal surface [graph (B) of FIG. 5], −10.42 mdeg on Cadmium metal surface [graph (C) of FIG. 5], and −13.87 mdeg on Nickel metal surface [graph (D) of FIG. 5]. This low intensity is due to degradation of alanine in $LiClO_4$ leading to achiral products. Therefore, CD measurements of the present disclosure illustrate that only L-alanine got adsorbed on the Nickel, Silver, Cadmium, and Gold metal surfaces and hence the enantiospecificity of the polycrystalline metal surfaces towards L-alanine was demonstrated.

Further, the enantiospecificity of the polycrystalline metal surfaces towards L-alanine was confirmed by UV spectroscopy, and FTIR spectroscopy.

Experiment 6: Process for Electrochemical Separation of Enantiomers of Methionine Using Nickel Electrode Surface 1M lithium perchlorate ($LiClO_4$) solution was mixed with the solution of 0.01M racemic methionine to form a first electrolyte. 0.01M racemic alanine consists of 0.005M D-methionine (50%) and 0.005M L-methionine (50%). The so formed first electrolyte was taken in an electrochemical cell which was further connected to the potentiostat. The electrochemical cell consists of working electrode i.e., Nickel electrode while silver (Ag)/silver chloride (AgCl) was used as reference electrode. The platinum coil worked as the auxiliary electrode. The working, reference, and auxiliary electrodes were polished with alumina solution before starting the measurements. The diameter of the electrode was 1 mm. The pH of the 1M lithium perchlorate ($LiClO_4$) solution containing 0.01M racemic methionine was maintained at 6.5. An IVIUMSTAT spectroelectrochemical workstation (Cyclic voltammetry) was employed for recording cyclic voltammogram (CV) of 0.01M racemic methionine in 1M lithium perchlorate ($LiClO_4$) solution. The enantiomeric separation process was carried out at room temperature. The so formed first electrolyte was electrolyzed in the electrochemical cell using saw-tooth current which leads to the adsorption of L-methionine on Nickel electrode surface (working electrode) and obtains first electrolyte with D-methionine in the cell. Further, the so obtained first electrolyte containing D-methionine was drained from the cell, followed by evaporation to separate D-methionine from the first electrolyte. Further, the drained electrochemical cell was re-filled with the solution of sodium chloride as second electrolyte. The polarity of the saw-tooth current was reversed to de-adsorb the L-methionine from said Nickel electrode surface into the second electrolyte. The second electrolyte having L-methionine was drained, followed by evaporation to separate L-methionine from the second electrolyte.

Further, the enantiospecificity of the polycrystalline metal surfaces towards L-methionine was confirmed by Circular Dichroism (CD) spectroscopy, UV spectroscopy, and FTIR spectroscopy.

The process of the present disclosure reactivates the working electrode having polycrystalline metal surface while desorption process so that these electrodes can be reused. Further, the amount of chiral reagents or solvents required in the system of the present disclosure is less. Therefore, the process of the present disclosure is simple, and economical.

Technical Advancements

The present disclosure described herein above has several technical advantages including, but not limited to, the realization of a process:
for enantiomeric separation of amino acid from a racemic mixture; and
that is simple and economical.

The embodiments as described herein above, and various features and advantageous details thereof are explained with reference to the non-limiting embodiments in the description. Descriptions of well-known aspects, components and molecular biology techniques are omitted so as to not unnecessarily obscure the embodiments herein.

The foregoing description of specific embodiments so fully reveal the general nature of the embodiments herein, that others can, by applying current knowledge, readily modify and/or adapt for various applications of such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein. Further, it is to be distinctly understood that the foregoing descriptive matter is to be interpreted merely as illustrative of the disclosure and not as a limitation.

Having described and illustrated the principles of the present disclosure with reference to the described embodiments, it will be recognized that the described embodiments can be modified in arrangement and detail without departing from the scope of such principles.

While considerable emphasis has been placed herein on the particular features of this disclosure, it will be appreciated that various modifications can be made, and that many changes can be made in the preferred embodiment without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

The invention claimed is:

1. A process for separating the enantiomers of an amino acid, selected from methionine, from a racemic mixture of said amino acid, said process comprising the following steps:
   i mixing 0.01 molar solution of the racemic amino acid with 1 molar solution of lithium perchlorate to form a first electrolyte;
   ii electrolyzing, using a saw-tooth current, the first electrolyte in an electrochemical cell in which the working electrode has a polycrystalline metal surface configured to adsorb the L-enantiomer of said amino acid and retaining the D-enantiomer in the first electrolyte;
   iii draining the first electrolyte containing D-enantiomer from said cell;
   iv separating the D-enantiomer from the first electrolyte;
   v re-filling the drained cell having the working electrode with the adsorbed L-enantiomer with a second electrolyte containing sodium chloride;
   vi reversing the polarity of the saw-tooth current fed to the cell to de-adsorb the L-enantiomer from said working electrode into said second electrolyte;
   vii draining said second electrolyte having the L-enantiomer dissolved therein; and
   viii separating the L-enantiomer from said second electrolyte.

2. The process as claimed in claim 1, wherein said racemic mixture of amino acid comprises 0.005 molar of L-enantiomer of said amino acid and 0.005 molar of D-enantiomer of said amino acid.

3. The process as claimed in claim 1, wherein said working electrode having polycrystalline metal surface is at least one selected from the group consisting of silver (Ag), gold (Au), cadmium (Cd), and nickel (Ni).

4. The process as claimed in claim 1, wherein D-enantiomer of said amino acid and L-enantiomer of said amino acid of step (iv) and step (viii) respectively, are separated by any one of the techniques selected from the group consisting of evaporation, solvent separation, and salting out.

5. The process as claimed in claim 1, wherein said sodium chloride solution is used as a second electrolyte.

* * * * *